United States Patent

Degner et al.

[11] 4,284,825
[45] Aug. 18, 1981

[54] 4-SUBSTITUTED BENZALDEHYDE-DIALKYLACETAL

[75] Inventors: Dieter Degner, Dannstadt-Schauernheim; Manfred Barl, Otterstadt; Hardo Siegel, Speyer, all of Fed. Rep. of Germany

[73] Assignee: BASF Aktiengesellschaft, Fed. Rep. of Germany

[21] Appl. No.: 89,952

[22] Filed: Oct. 31, 1979

[30] Foreign Application Priority Data

Nov. 8, 1978 [DE] Fed. Rep. of Germany ....... 2848397

[51] Int. Cl.³ .......................................... C07C 43/307
[52] U.S. Cl. .................................. 568/592; 560/132; 204/59 R
[58] Field of Search ......................................... 568/592

[56] References Cited

U.S. PATENT DOCUMENTS 3,773,630 11/1973 Popescu ........................... 568/592 X Primary Examiner—Bernard Helfin
Attorney, Agent, or Firm—Keil & Witherspoon

[57] ABSTRACT 4-substituted benzaldehyde-dialkylacetals of the formula

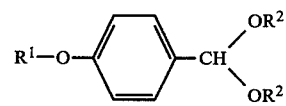

where $R^1$ is one of the radicals $CH_2=CH-CH_2-$,

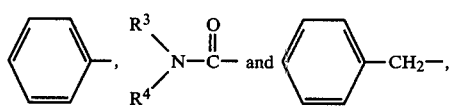

$R^2$ is alkyl and $R^3$ and $R^4$ are hydrogen or alkyl, and a process for the electrochemical preparation of these compounds.

1 Claim, No Drawings

4-SUBSTITUTED BENZALDEHYDE-DIALKYLACETAL

The present invention relates to novel 4-substituted benzaldehyde-dialkylacetals and to a process for the electrochemical preparation of these benzaldehydedialkylacetals.

The novel benzaldehyde-dialkylacetals have the formula

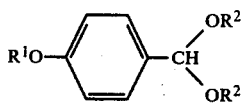   I where $R^1$ is one of the radicals

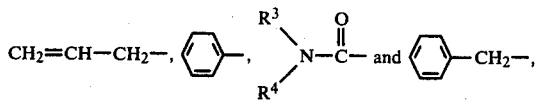

$R^2$ is alkyl of 1 to 4 carbon atoms and $R^3$ and $R^4$ are hydrogen or alkyl of 1 to 6 carbon atoms.

The novel benzaldehyde-dialkylacetals of the formula I may be prepared, for example, by electrochemical oxidation of a 4-substituted methylbenzene of the general formula

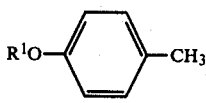   II where $R^1$ has the above meaning, in the presence of an alcohol of the formula $$R^2OH \qquad III$$

where $R^2$ has the above meaning, and of a conductive salt.

Examples of starting compounds of the formula II are p-benzyloxytoluene, p-phenoxytoluene, 4-methylphenyl-N,N-dimethylcarbamate and p-allyloxytoluene. Preferred alcohols of the formula III are methanol and ethanol.

The process according to the invention may be carried out either in a compartmented or in a non-compartmented cell. The electrolyte used is a solution of the substituted methylbenzene in the alcohol employed, which solution contains a conductive salt. Examples of conductive salts used are the conductive salts conventionally employed in electrochemistry. Examples of very suitable salts are those which are soluble in the solution to be electrolyzed and are substantially stable under the process conditions. Specific examples of particularly suitable conductive salts are fluorides, eg. KF, tetrafluoborates, eg. $Et_4NBF_4$, perchlorates, eg. $Et_4NClO_4$, sulfates, eg. $Et_4NSO_4Et$, alcoholates, eg. $NaOCH_3$, and hydroxides, eg. KOH.

In the process according to the invention, the composition of the electrolyte can be selected within a wide range. For example, the electrolyte solutions used may have the following composition:
5-50% by weight of methylbenzene of the formula II
50-95% by weight of alcohol of the formula III
0.5-15% by weight of conductive salt.

To improve the solubility of the methylbenzenes, cosolvents, which are substantially stable under the process conditions, may additionally be used where necessary. Examples of such co-solvents are nitriles, eg. acetonitrile, halohydrocarbons, eg. methylene chloride, ethers, eg. dimethoxyethane, and ketones, eg. acetone.

Anode materials which may be employed in the process according to the invention are any electrode materials which are stable under the experimental conditions. Examples of suitable anode materials are graphite, graphite-filled plastics, noble metals, eg. platinum and gold, and titanium electrodes coated with a noble metal. Examples of suitable cathodes are graphite, iron, steel, lead or noble metal electrodes. The current density and conversion may be selected within a wide range. The current density may be, for example, 1–20 $A/dm^2$, and the actual electrolysis is carried out with, for example, 2–15 Faraday per mole of starting compound. The electrolysis temperature may be, for example, from 0° to 60° C.

As a rule, the material obtained from the electrolysis is worked up by distillation. Excess alcohol and any residual starting material is removed from the acetal by distillation and may be recycled to the electrolysis. The substituted benzaldehyde-dialkylacetals can then be purified further, for example by rectification. The conductive salt used can, prior to the purification of the acetals by distillation, be separated from the acetals by, for example, filtration, and be recycled to the electrolysis.

The substituted benzaldehyde-acetals, and the benzaldehydes preparable from these by conventional methods, are intermediates for crop protection agents, scents and aromatics. 4-Benzyloxybenzaldehyde-dimethylacetal can be easily converted to 4-hydroxybenzaldehyde by reaction with acids. 4-Hydroxybenzaldehyde is an intermediate for the preparation of 4-hydroxyphenylglycine, which is employed for the synthesis of semi-synthetic antibiotics, eg. amoxillin.

EXAMPLE 1

Preparation of 4-benzyloxybenzaldehyde-dimethylacetal.

| Apparatus: | Non-compartmented cell with 7 electrodes; electrode spacing: 0.5 mm |
|---|---|
| Anodes: | Graphite |
| Electrolyte: | 792 g of 4-methylphenyl benzyl ether |
| | 25 g of KF |
| | 2,137 g of methanol |
| Cathodes: | Graphite |
| Temperature: | 35–40° C. |
| Current density: | 4.7 $A/dm^2$ |

The electrolysis is carried out with 5 F/mole of 4-methylphenyl benzyl ether. During the electrolysis, the electrolyte is pumped over a heat exchanger. Working-up: After completion of the electrolysis, the methanol is distilled off, the KF (22 g) is filtered off and the residue is subjected to fractional distillation under 1-2 mm Hg and 160°–180° C. This gives 27.8 g of unconverted 4-methylphenyl benzyl ether and 617.9 g of 4-benzyloxybenzaldehyde-dimethylacetal, corresponding to 62.1% yield of material and 47.9% current efficiency.

EXAMPLE 2

Preparation of 4-allyloxybenzaldehyde-dimethylacetal

| | |
|---|---|
| Apparatus: | Non-compartmented cell with 7 electrodes; electrode spacing: 0.5 mm |
| Anodes: | Graphite |
| Electrolyte: | 296 g of 4-methylphenyl allyl ether<br>25 g of KF<br>2,375 g of methanol |
| Cathodes: | Graphite |
| Temperature: | 25–28° C. |
| Current density: | 5.4 A/dm$^2$ |

The electrolysis is carried out with 13.4 F/mole of 4-methylphenyl allyl ether. During the electrolysis, the electrolyte is pumped over a heat exchanger. Working-up: After completion of the electrolysis, the methanol is distilled off, the KF (22 g) is filtered off and the residue is subjected to fractional distillation under 1-2 mm Hg and 130°–140° C. This gives 151 g of 4-allyloxybenzaldehyde-dimethylacetal, corresponding to a material yield of 36.3% and a current efficiency of 10.8%.

EXAMPLE 3

Preparation of 4-phenoxybenzaldehyde-dimethylacetal

| | |
|---|---|
| Apparatus: | Non-compartmented cell with 7 electrodes; electrode spacing: 0.5 mm |
| Anodes: | Graphite |
| Electrolyte: | 100 g of 4-methylphenyl phenyl ether<br>25 g of KF<br>2,375 g of methanol |
| Cathodes: | Graphite |
| Temperature: | 24–30° C. |
| Current density: | 5.4 A/dm$^2$ |

The electrolysis is carried out with 11 F/mole of 4-methylphenyl phenyl ether. During the electrolysis, the electrolyte is pumped over a heat exchanger. Working-up: After completion of the electrolysis, the methanol is distilled off, the KF (23 g) is filtered off and the residue is subjected to fractional distillation under 0.5–1 mm Hg and 110°–150° C. This gives 52 g of 4-phenoxybenzaldehyde-dimethylacetal, corresponding to a material yield of 39.2% and a current efficiency of 14.3%.

EXAMPLE 4

Preparation of [(4-dimethoxymethyl)-phenyl]-N,N-dimethylcarbamate

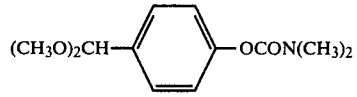

| | |
|---|---|
| Apparatus: | Non-compartmented cell with 7 electrodes; electrode spacing: 0.5 mm |
| Anodes: | Graphite |
| Electrolyte: | 330 g of p-cresyl-N,N-dimethylcarbamate,<br>2,370 g of methanol<br>25 g of KF |
| Cathodes: | Graphite |
| Temperature: | 25–30° C. |
| Current density: | 4.7 A/dm$^2$ |

The electrolysis is carried out with 10 F/mole of p-cresyl-N,N-dimethylcarbamate. During the electrolysis, the electrolyte is pumped over a heat exchanger. Working-up: After completion of the electrolysis, the methanol is distilled off, the KF (23 g) is filtered off and the residue is subjected to fractional distillation under 2 mm Hg and 60°–170° C. This gives 97 g of p-cresol, 52 g of unconverted p-cresyl-N,N-dimethylcarbamate and 150 g of [(4-dimethoxymethyl)-phenyl]-N,N-dimethylcarbamate, corresponding to a material yield of 40.4%.

We claim:

1. 4-Benzyloxybenzaldehyde-dimethylacetal.

* * * * *